United States Patent
Duerig et al.

(10) Patent No.: US 6,179,878 B1
(45) Date of Patent: Jan. 30, 2001

(54) COMPOSITE SELF EXPANDING STENT DEVICE HAVING A RESTRAINING ELEMENT

(76) Inventors: Thomas Duerig, 41790 Vargas Rd., Fremont, CA (US) 94539; Dieter Stockel, 960 Black Mountain Ct., Los Altos, CA (US) 94024

(*) Notice: Under 35 U.S.C. 154(b), the term of this patent shall be extended for 0 days.

(21) Appl. No.: 09/172,053

(22) Filed: Oct. 14, 1998

Related U.S. Application Data

(62) Division of application No. 08/735,128, filed on Oct. 22, 1996.

(51) Int. Cl.$^7$ .................................................. A61F 2/06
(52) U.S. Cl. ..................... 623/902; 623/1.13; 623/1.18; 623/1.2; 623/1.12
(58) Field of Search .................................. 623/1, 11, 12, 623/1.1, 1.12, 1.13, 1.18, 1.19, 1.2, 902, 903; 606/108, 191, 194, 195, 198

(56) References Cited

U.S. PATENT DOCUMENTS

| | | | |
|---|---|---|---|
| 5,403,341 | * 4/1995 | Solar | 606/198 |
| 5,637,113 | * 6/1997 | Tartaglia et al. | 623/1 |
| 5,653,747 | * 8/1997 | Dereume et al. | 623/1 |
| 5,667,523 | * 9/1997 | Bynon et al. | 623/1 |
| 5,700,286 | * 12/1997 | Tartaglia et al. | 623/1 |
| 5,741,325 | * 4/1998 | Chaikof et al. | 623/1 |
| 5,779,732 | * 7/1998 | Amundson | 623/1 |
| 5,824,046 | * 10/1998 | Smith et al. | 623/1 |
| 5,876,432 | * 3/1999 | Lau et al. | 623/1 |
| 5,897,589 | * 4/1999 | Cottenceau et al. | 623/1 |

* cited by examiner

Primary Examiner—Mickey Yu
Assistant Examiner—Tram A. Nguyen
(74) Attorney, Agent, or Firm—Dean Garner

(57) ABSTRACT

A composite stent device comprises a shape memory alloy stent sleeve which is treated so that it can exert an outward force on a lumen in which the stent device is to be deployed, and a restraint element which restricts the maximum transverse dimension to which the stent sleeve can expand outwardly. The restraint sleeve can minimize damage to a lumen by a stent located within it. It can be arranged to allow the stent device to be deformed in a bending mode, for example when the lumen in which the device is located is subjected to a transverse flattening deformation, relying on the enhanced elastic properties of the shape memory alloy stent sleeve to recover to the open, generally rounded configuration.

2 Claims, 7 Drawing Sheets

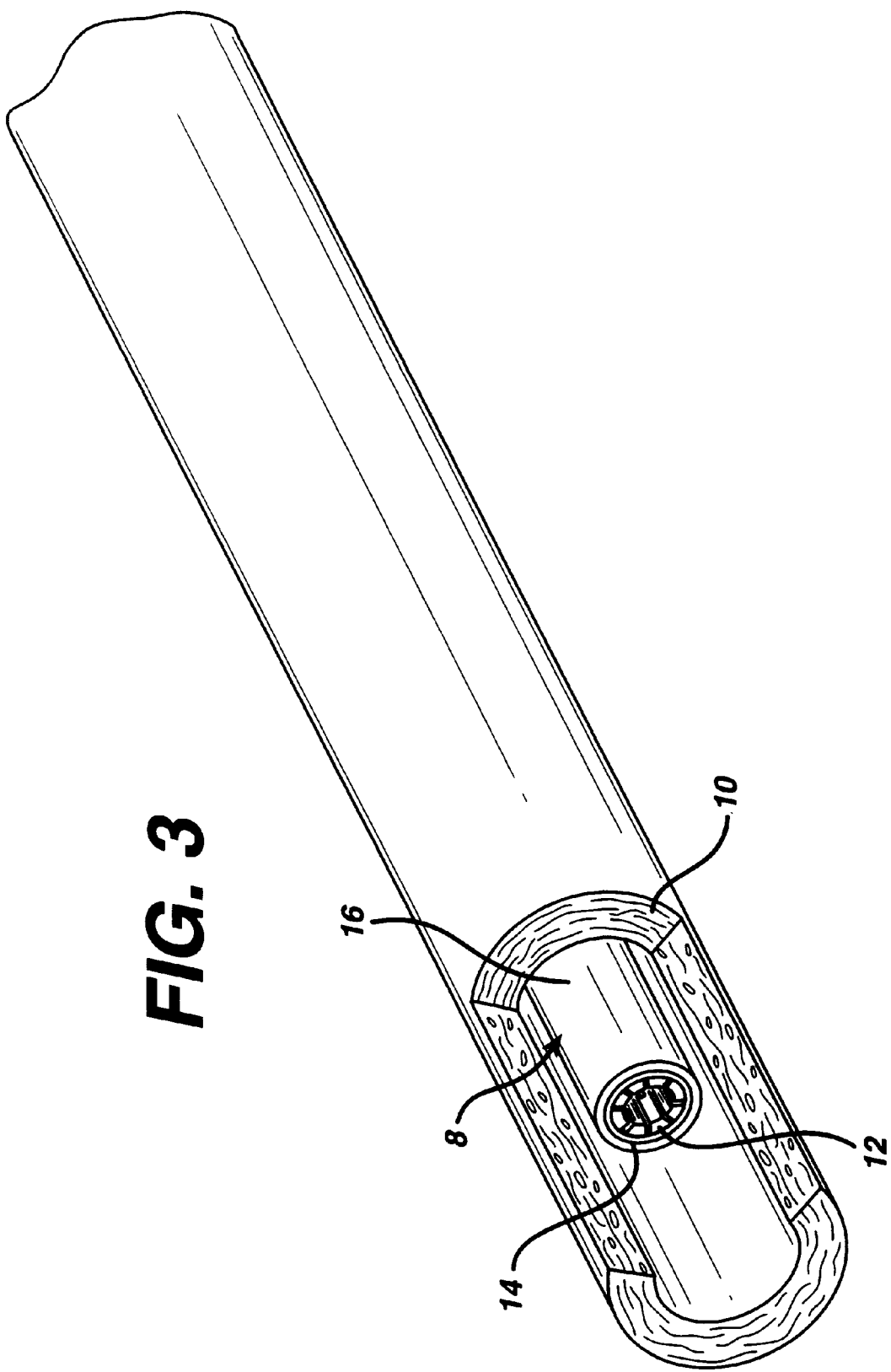

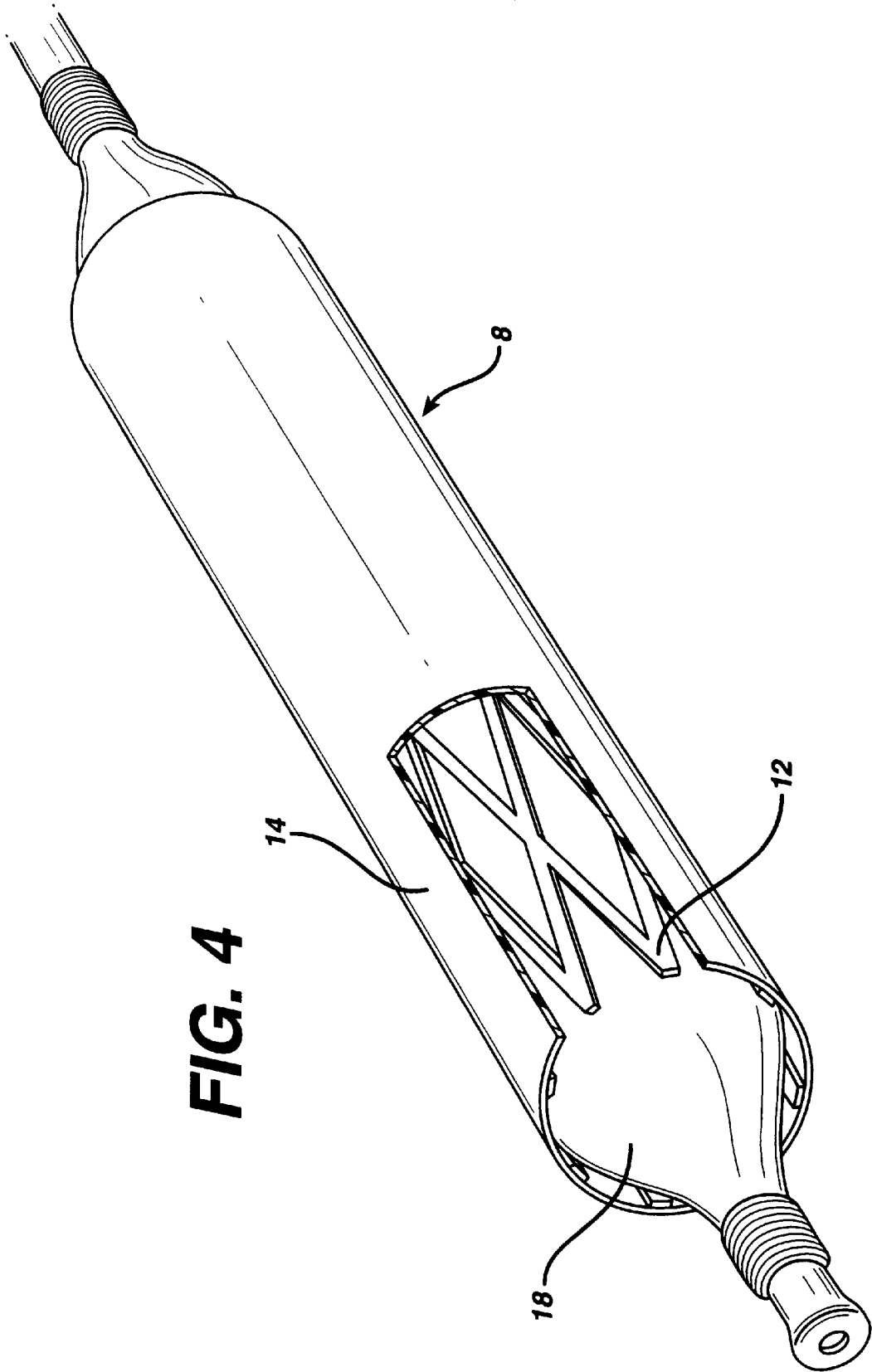

COMPOSITE SELF EXPANDING STENT DEVICE HAVING A RESTRAINING ELEMENT

This is a division of Ser. No. 08/735,128 filed Oct. 22, 1996.

BACKGROUND OF THE INVENTION

This invention relates to a composite stent, to a stent assembly which includes a composite stent device, and to a method of making a stent.

Stents are used in lumens in a human or animal body. When properly positioned in a lumen, a stent can contact the wall of the lumen to support it or to force the wall outwardly.

Stents can be made from a material which enable the stent to be compressed transversely elastically so that they can then recover outwardly when the compressing force is removed, into contact with the wall of the lumen. The enhanced elastic properties available from shape memory alloys as a result of a transformation between martensite and austenite phases of the alloys make them particularly well suited to this application. The nature of the superelastic transformations of shape memory alloys is discussed in "Engineering Aspects of Shape Memory Alloys", T W Duerig et al, on page 370, Butterworth-Heinemann (1990). Subject matter disclosed in that document is incorporated in this specification by this reference to the document. A principal transformation of shape memory alloys involves an initial increase in strain, approximately linearly with stress. This behaviour is reversible, and corresponds to conventional elastic deformation. Subsequent increases in strain are accompanied by little or no increase in stress, over a limited range of strain to the end of the "loading plateau". The loading plateau stress is defined by the inflection point on the stress/strain graph. Subsequent increases in strain are accompanied by increases in stress. On unloading, there is a decline in stress with reducing strain to the start of the "unloading plateau" evidenced by the existence of an inflection point along which stress changes little with reducing strain. At the end of the unloading plateau, stress reduces with reducing strain. The unloading plateau stress is also defined by the inflection point on the stress/strain graph. Any residual strain after unloading to zero stress is the permanent set of the sample. Characteristics of this deformation, the loading plateau, the unloading plateau, the elastic modulus, the plateau length and the permanent set (defined with respect to a specific total deformation) are established, and are defined in, for example, "Engineering Aspects of Shape Memory Alloys", on page 376.

Non-linear superelastic properties can be introduced in a shape memory alloy by a process which involves cold working the alloy for example by a process that involves pressing, swaging or drawing. The cold working step is followed by an annealing step while the component is restrained in the configuration, resulting from the cold working step at a temperature that is sufficiently high to cause dislocations introduced by the cold working to combine and dislocations to align. This can ensure that the deformation introduced by the cold work is retained.

The technique for introducing superelastic properties can be varied from that described above. For example, instead of subjecting the alloy to a heat treatment while restrained in the deformed configuration, the alloy could be deformed beyond a particular desired configuration and then heat treated such that there is a thermally induced change in configuration of the kind discussed below, the change taking the configuration towards the particular desired configuration. Introduction of the superelastic properties might also involve annealing at high temperature (for example towards the recrystallisation temperature of the alloy), followed by rapid cooling and then a heat treatment at a lower temperature.

The properties of shape memory alloys can also involve thermally induced changes in configuration in which an article is first deformed from a heat-stable configuration to a heat-unstable configuration while the alloy is in its martensite phase. Subsequent exposure to increased temperature results in a change in configuration from the heat-unstable configuration towards the original heat-stable configuration as the alloy reverts from its martensite phase to its austenite phase. It is known from U.S. Pat. No. 5,197,978 to make use of the thermally induced change in configuration of an article made from a shape memory alloy in a stent.

The use of a stent which is formed from a shape memory alloy is attractive because it can exert an outward force on the lumen in which it is to be used continuously after it has been deployed in the desired location. This allows the lumen to be maintained open. It can also mean that the stent remains in the desired location. The enhanced elastic properties of shape memory alloys also allow a stent to move and flex with a lumen after installation. This can be particularly important when a stent is positioned in an exposed lumen, such as a femoral or carotid artery. Forces applied externally to these vessels can cause them to flatten substantially from their normally round cross-section.

It is important that the configuration of a shape memory alloy stent towards which it attempts to recover while in the lumen is properly selected. If that configuration is too small, the stent will be loose in the lumen; this can result in the lumen not being properly supported by the stent and in the stent becoming dislodged from the desired location. If the configuration towards which the stent attempts to recover is too big, the residual force exerted by the stent on the lumen can be too high; it is thought that this could be undesirable in some situations because of a risk of damage to the lumen.

SUMMARY OF THE INVENTION

The present invention provides a composite stent device which includes a restraint element which can be deformed plastically and which can restrict the maximum transverse dimension to which the shape memory stent sleeve can expand outwardly.

Accordingly, in one aspect, the invention provides a composite stent device which comprises (a) a shape memory alloy stent sleeve which is treated so that it can exert an outward force on a lumen in which the stent device is to be deployed, and (b) a restraint element which restricts the maximum transverse dimension to which the stent sleeve can expand outwardly.

The stent device of the invention can be used in a lumen where the size of the lumen is not known accurately. The transverse dimension to which the stent device expands in the lumen can be adjusted by deformation of the restraint element, until the transverse dimension is large enough to ensure that an appropriate force is exerted on the lumen. The deformation of the stent device will generally take place while it is located in the lumen. The deformation involves deformation of the restrained element, allowing the stent sleeve to recover further towards its relaxed configuration in which recovery forces are resolved. This can be achieved by means of an expansion device which, when positioned within the stent device, can expand the device by plastic deformation of the restraint element. Accordingly, in another aspect, the invention provides a stent assembly which comprises (a) a stent device of the type discussed above, and (b) an expansion device which, when positioned within the stent device, can increase the maximum transverse dimension to which the device can expand by plastic deformation of the restraint element. An example of a suitable expansion device is an inflatable balloon.

As well as restricting the maximum transverse dimension to which the stent sleeve can expand outwardly, the restraint element should preferably be capable of being deformed transversely with the stent sleeve, for example under force applied externally to the lumen in which the stent device is located. It is possible for the restraint element to tolerate such transverse deformation and to reform elastically under the restoring force provided by the stent sleeve, while restricting the maximum transverse dimension of the stent device.

The presence of the shape memory alloy stent sleeve in the device of the invention has the advantage that the device continues to exert an outward force against the lumen after deployment, to support the lumen and to prevent the device from becoming dislodged from the desired location. Generally, the shape memory alloy component will exert the outward force as a result of a treatment which relies on the enhanced elastic properties which they can be made to exhibit, sometimes referred to as superelastic or pseudoelastic properties. Thus, for example, a stent sleeve might be formed in a initial configuration towards which it is to recover, and then deformed inwardly to a deformed configuration in which it is constrained by means of a restraint element, the assembly of the shape memory and restraint elements providing the stent device of the present invention. The diameter of the device when so constrained should be less than the smallest lumen diameter through which the device has to pass when being moved to the intended location in which it is to be deployed.

A constraining component may be used to constrain the stent device of the invention in the configuration selected for delivery to a desired location in a lumen, in addition to the constraining effect provided by the restraint sleeve. For example, the device may be compressed transversely and held in that configuration by means of a delivery catheter.

For some applications, the composite stent device will be designed so that the shape memory alloy stent sleeve exerts a force against the restraint element and the lumen following a thermally initiated change in phase from its martensite phase to its austenite phase. This change can result from exposure of the sleeve to the temperature of the human or animal body. The use of a stent sleeve that has been made to exert a force in this way can have the advantage of preventing undesirable deformation of the restraining sleeve prior to use.

The composite stent device of the invention can be delivered to a desired location in a lumen in a human or animal body by means of a delivery device such as a catheter. The restraint element in the stent device can assist in deployment of the stent device from the catheter (for example by means of a wire, rod or other pushing implement) in that the transverse force which is exerted by the device against the catheter is controlled, restricting frictional effects between the device and the catheter and deformation of the catheter by the device. The catheter can also be used to deliver the inflatable balloon or other device by which the restraint element is expanded to set the desired configuration for the deployed device.

The stent sleeve can be located generally within the restraint element; preferably, the restraint element is at least as long as the stent sleeve so that the stent sleeve can be located wholly within the restraint element.

The shape memory alloy used in the stent sleeve can be a binary alloy, generally based on nickel—titanium. Suitable binary alloys include those in which the nickel content is at least about 50 at. %, preferably at least about 50.5 at. %. The nickel content will usefully be less than about 52 at. %, preferably less than about 51 at. %. The sleeve can be formed from other Ni—Ti based alloys, including alloys with ternary and quaternary additions. Examples of elements that can be incorporated in the alloy include Fe, Co, Cr, Al, Cu and V. Added elements can be present in amounts upto about 10 at. %, preferably upto about 5 at. %.

Preferably, the stent sleeve has an open lattice structure, which might comprise for example slits, or bigger openings. A stent sleeve with a lattice structure can be formed by cutting a tube. It might also be formed from wire using an appropriate bonding technique at points where wires cross. Preferably, the deformation step of the method involves reducing the transverse dimension of the stent device by changing the shape of the lattice. The deformation can comprise applying a compressive force to the device, generally transversely. This can result in a reduction in the transverse dimension of the device as a result of a bending deformation of the component arms which define the apertures in the lattice structure. The width of the arms will often be generally less than about 1.0 mm, preferably less than about 0.8 mm, more preferably less than about 0.5 mm, especially less than about 0.25 mm. When the arms are not parallel to the direction along which the force is applied, the bending can be between arms at the points at which they meet; the arms themselves can often remain substantially straight. In a stent sleeve in which the lattice structure defines a plurality of diamond shape openings, the deformation can then involve flattening the diamonds. When the arms defining the apertures in the lattice structure are parallel or nearly parallel to the direction along which the force is applied, the deformation can involve bending the arms between the points at which adjacent arms meet.

The deformation of the stent sleeve will be from a configuration which represents the largest anticipated size of lumen into which the stent device is to be used, the device then being capable of expanding outwardly to engage the walls of the stent with outward deformation of the restraint element as necessary.

The stent sleeve can be deformed elastically by transverse compression. For example, it can be compressed by passing the sleeve through a tapered aperture. Alternatively or in addition, the sleeve can be deformed by application of an elongating force, generally longitudinally of the sleeve. When the sleeve has an open lattice structure with arms defining the apertures in the lattice non-parallel to the longitudinal axis of the sleeve, the deformation will tend to change the shape of the apertures by bending the arms at the points at which they meet; the arms themselves can often remain substantially straight. In a sleeve in which the lattice structure defines a plurality of diamond shape openings, the deformation can then involve flattening the diamonds.

Preferably, the stent sleeve is made by a process which involves removing material from a sheath-like object, leaving an open lattice structure that is capable of appropriate deformation. The nature of the removal process will depend on the material of the sheath-like object. For example, the removal process may involve one or more of cutting, melting and vaporising the material. Preferably, the removal process can involve use of a laser cutting tool. Other techniques which might be used for forming the pattern in the material include electrical discharge machining, stamping, cutting, and etching (especially photoetching).

Preferably, the sheath-like object from which the stent sleeve is formed is a tubular object, especially a cylindrical tube with a circular cross-section.

While the removal process referred to above is preferred for forming the stent sleeve, it might be formed in other ways, for example from wire formed in a helical configuration, or by welding pieces of wire together. The sleeve could also be made from sheet material which can be formed into a tube, for example by folding and welding.

Preferably, the wall thickness of the material of the stent sleeve less than about 1.5 mm, more preferably less than about 0.5 mm. Preferably, the wall thickness is at least about 0.05 mm, more preferably at least about 0.1 mm.

Preferably, the maximum transverse dimension of the stent sleeve (which will be its diameter when the stent device has a circular cross-section) is not more than about 40 mm, more preferably not more than about 20 mm, especially not more than about 10 mm. Preferably, its minimum transverse dimension is at least about 0.5 mm, more preferably at least about 1 mm.

The material and configuration of the restraint element will be selected according to (a) the forces that will be exerted against it by the stent sleeve and (b) the nature of the technique used to expand it. It should be designed so that it can be appropriately expanded (generally involving plastic deformation) by the expansion device but should be capable of appropriately restraining the transverse expansion of the stent sleeve. It should also be sufficiently dimensioned so as not to occlude the lumen undesirably, and not to prevent the lumen from being bent. The thickness of the restraint element should be sufficient to provide the necessary restraint against transverse expansion of the stent sleeve, while preferably also being able to bend elastically, for example when the stent device is subjected to a flattening force as might happen in an exposed lumen such as a femoral or carotid artery. Such a flattening deformation can be recovered relying on the enhanced elastic properties of a shape memory alloy, as discussed above.

The restraint element can be in the form of a sleeve which the stent sleeve can fit into. Such a restraining sleeve can have a continuous outer surface such as might be formed by extrusion or folding a continuous sheet. It might otherwise be foraminous in the form of a mesh or perforated sheet. The restraint element need not be a discrete component. For example, it could be made from strips or wires wrapped around the perimeter of the stent sleeve. The restraint element might be provided as a part of the stent sleeve. For example, a restraint element formed from wires might be formed in the stent sleeve, which can be deformed plastically during expansion of the stent device.

When the restraint sleeve is provided by woven wires or other elements, the elements need not extend completely around the stent sleeve. The deformation of such a restraint element will then involve slipping of the elements within the weave, possibly but not necessarily together with plastic deformation of the material of the wires.

When the restraint sleeve is provided by one or more wires or other elements that are wrapped around the stent sleeve, for example helically, the elements should be selected with an appropriate thickness to restrict transverse expansion of the stent sleeve while also permitting transverse flattening of the device. For example a stainless steel wire of about 0.02 mm thickness can be used in a restraint for a 3 mm diameter stent sleeve.

The restraint element can be formed from a polymeric material. Examples of suitable materials include polyolefins, halogenated polyolefins (especially PTFE), polyesters, polyamides, natural human or animal tissue, and so on. Polyethylene and PTFE can be particularly suitable for many applications. Metallic materials can be used for the restraint element such as stainless steels and titanium. The restraint element can be continuous along the length of the stent sleeve with a tubular configuration. It might have openings in it or be discontinuous, for example in the form of bands or threads provided sufficiently close together to provide the desired restraint for the stent sleeve. A restraint element formed from a polymeric material can be formed with a tubular configuration, for example by extrusion. A restraint element formed from a metal might be provided as a mesh.

A restraint element formed from a polymeric material such as a polyester, for use with a stent sleeve having an external diameter before deformation (and which it attempts to recover to) of greater than 3 mm and wall thickness of about 0.2 mm, will typically have a wall thickness of about 0.01 to 0.2 mm, depending on the mechanical properties of the material that is used.

INTRODUCTION TO THE DRAWINGS

FIG. 3 is an isometric view of a stent comprising the sleeve shown in FIGS. 1 and 2 and a restraining sleeve, being delivered to a desired location in a lumen in a catheter.

FIG. 4 is an isometric view, partially in section, of the stent after delivery with an expansion device located within it to expand it by plastic deformation of the restraint element.

DESCRIPTION OF PREFERRED EMBODIMENTS

Figure 1:
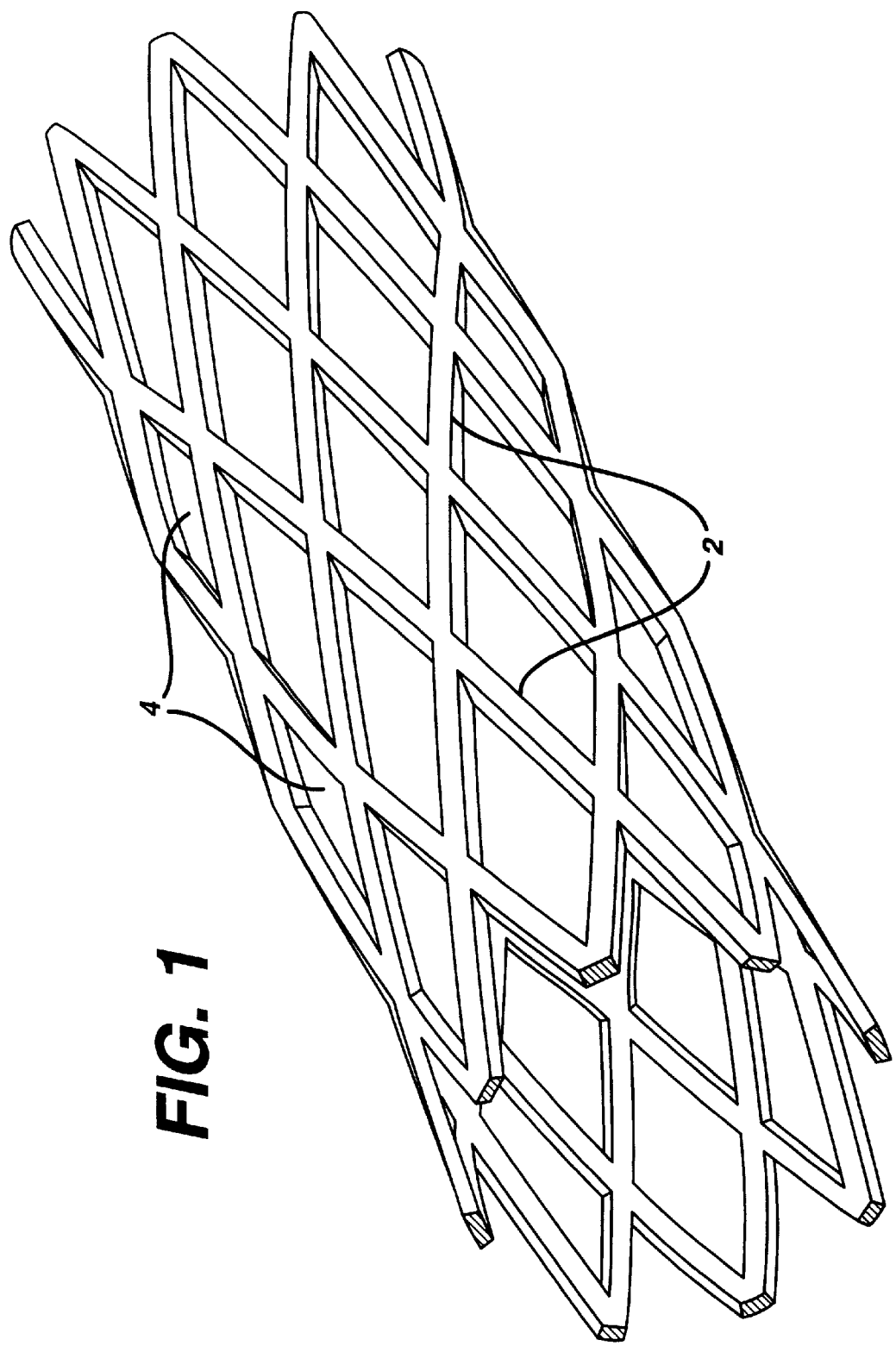
FIG. 1 is an isometric view of a stent sleeve for use in the stent device of the invention, which has been produced with an appropriate configuration but before any thermal or mechanical treatment intended to give the sleeve the desired deformation behaviour.

FIG. 1 shows a stent sleeve which can be used in the stent device of the invention. The sleeve has an open lattice structure defined by arms 2. Openings 4 between the arms extend through the thickness of the sleeve. The sleeve is formed by cutting a tube, for example using a YAG laser cutting tool. The sleeve is formed from a binary nickel—titanium alloy containing about 50.8 at. % Ni. The sleeve is formed from a binary nickel—titanium alloy containing about 50.8 at. % Ni. The transverse dimension of this sleeve can be changed by deformation of the sleeve. The deformation results in changes in the shape of the openings 4, as a result of bending the arms at the point at which they meet. As formed from a tube, the sleeve has an internal transverse dimension of about 4 mm. The wall thickness of the tube and therefore the thickness of each of the arms 2 is about 0.3 mm.

Figure 2:
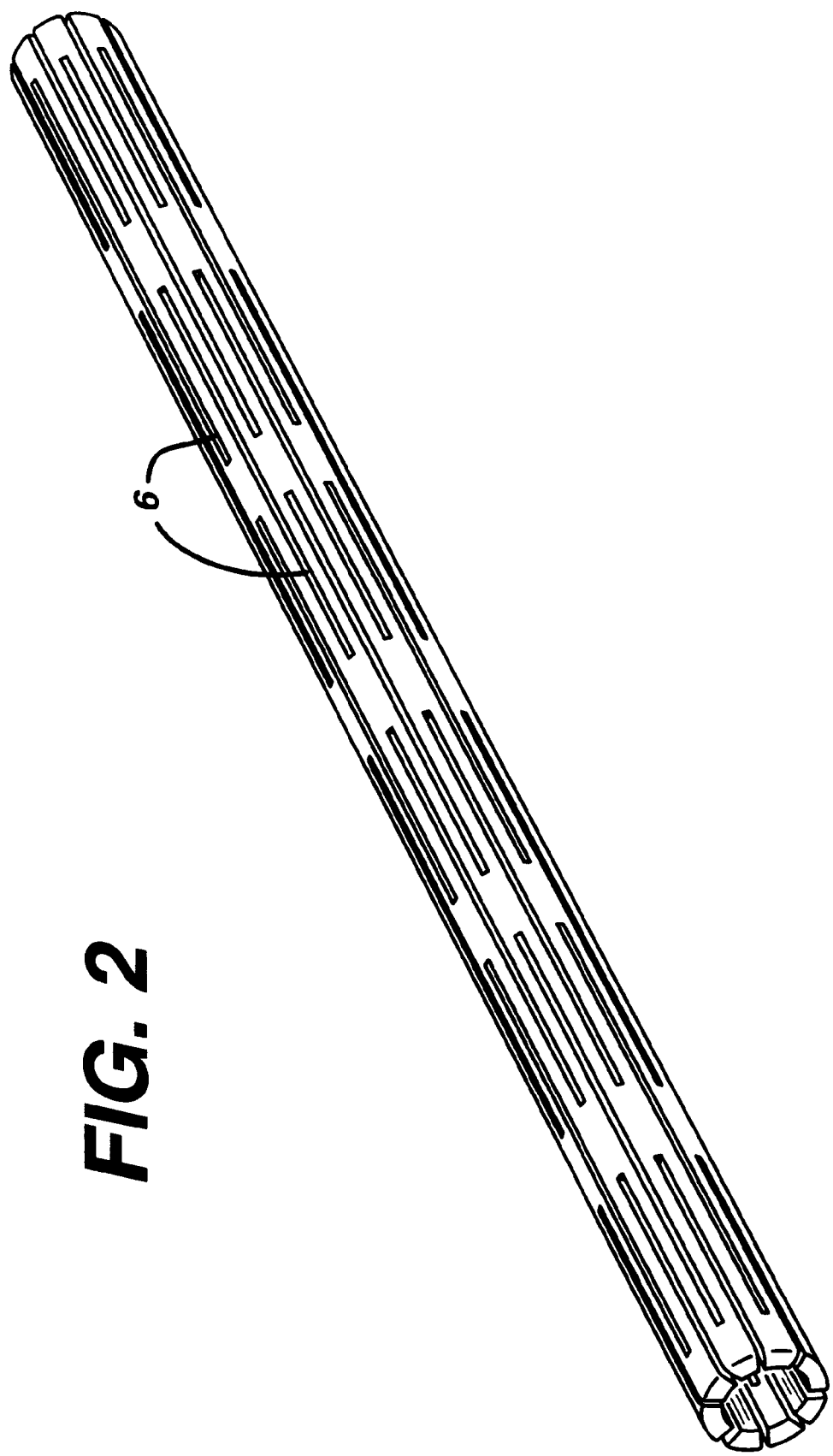
FIG. 2 is an isometric view of the sleeve shown in FIG. 1, after deformation from its initial configuration to the configuration in which it can be inserted into a restraint element for deployment.

FIG. 2 shows the sleeve shown in FIG. 1 after it has been deformed. The deformation involves reduction in the transverse dimension of the sleeve. As a result, the openings 4 in the sleeve as shown in FIG. 1 effectively become slits 6. The sleeve can be deformed in this way by application of a longitudinal force at opposite ends of the sleeve. The sleeve is deformed from the configuration shown in FIG. 1 towards that shown in FIG. 2 under such conditions that the deformation takes place elastically. The sleeve is then able to revert towards the configuration shown in FIG. 1 when appropriately positioned in a lumen.

Figure 3A:
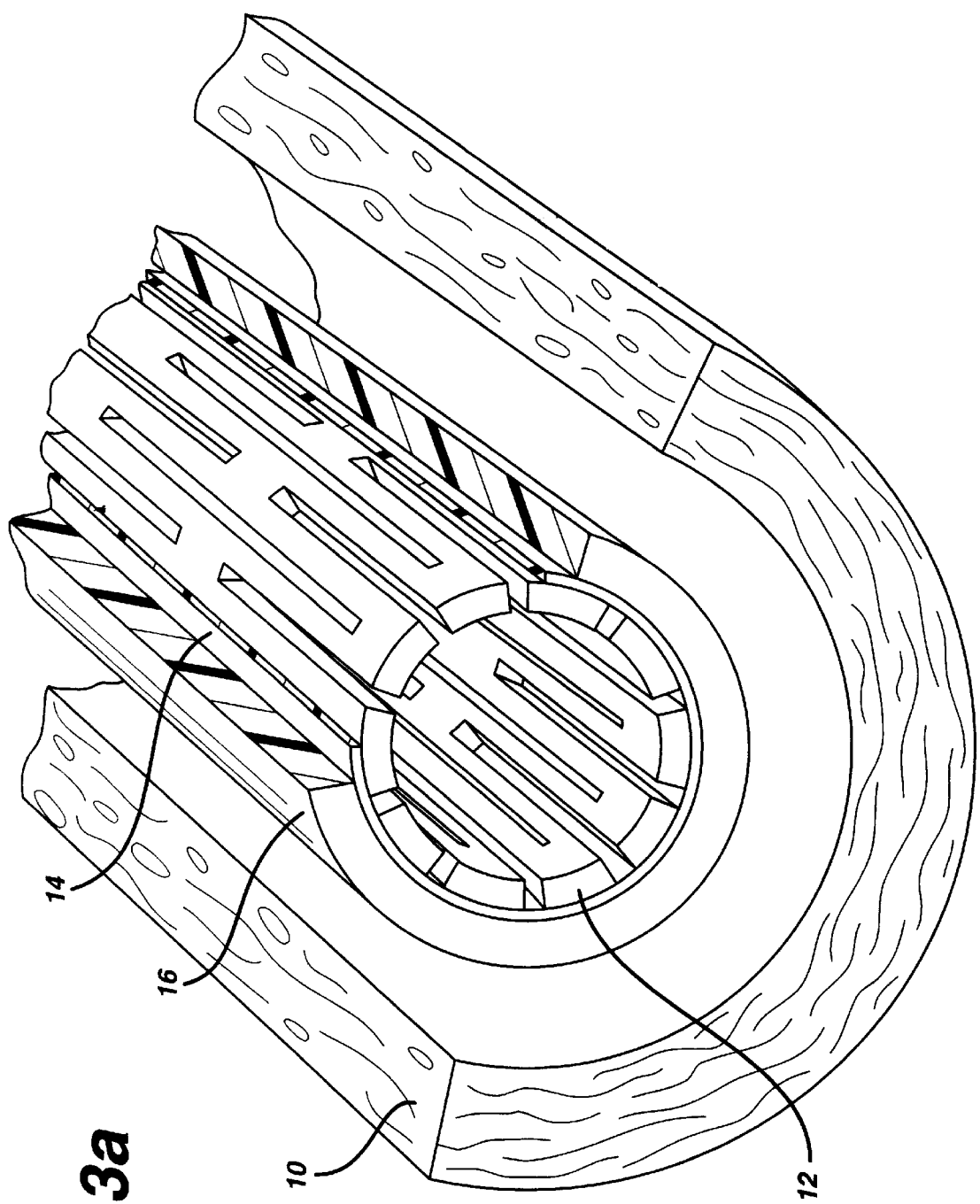
FIG. 3a is an expanded view, partially in section, through the stent as shown in FIG. 3.

FIGS. 3 and 3a show the stent device 8 of the invention being deployed in a lumen 10 such as a blood vessel. The stent sleeve 12 is retained in the deformed configuration shown in FIG. 2 by means of a restraint 14, which restricts the maximum transverse dimension to which the stent sleeve can expand outwardly, from the configuration shown in FIG. 2 towards that shown in FIG. 1. The restraint comprises a sleeve formed from medical grade polyethylene, with a wall thickness of about 0.1 mm. Use of a sleeve with this wall thickness allows the restraint to restrict the maximum transverse dimension of the stent sleeve, while allowing the stent device to be flattened at least partially. When so restrained, the stent device including the stent sleeve can be moved along the lumen using conventional techniques such as involving a catheter 16.

Once located appropriately in the lumen, the stent device shown in FIG. 3 is discharged from a catheter using known techniques, for example by means of an inserted pusher rod. The device of the invention can be expanded, into contact with the internal surface of the lumen, by means of an appropriate inflatable balloon 18, as shown in FIG. 4. Inflation of the balloon results in outward deformation of the stent sleeve 12, in the direction of its elastic recovery towards the configuration shown in FIG. 1. At the same time, the restraint sleeve 14 is expanded plastically.

Figure 5:
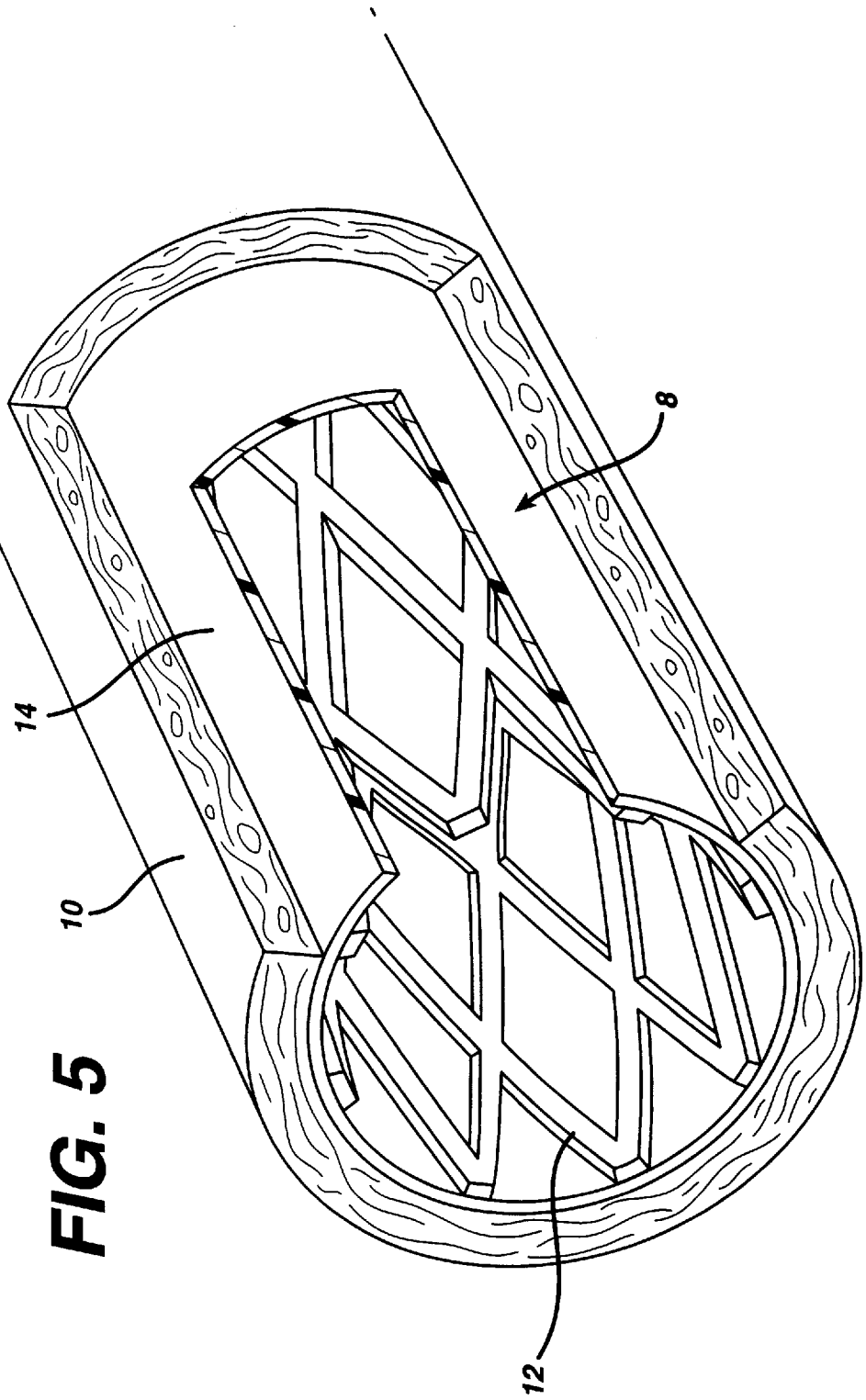
FIG. 5 is an isometric view, partially in section, of the stent device located in the lumen after completion of the delivery process.

FIG. 5 shows the device 8 installed in a lumen, after expansion by an inserted balloon.

Figure 6:
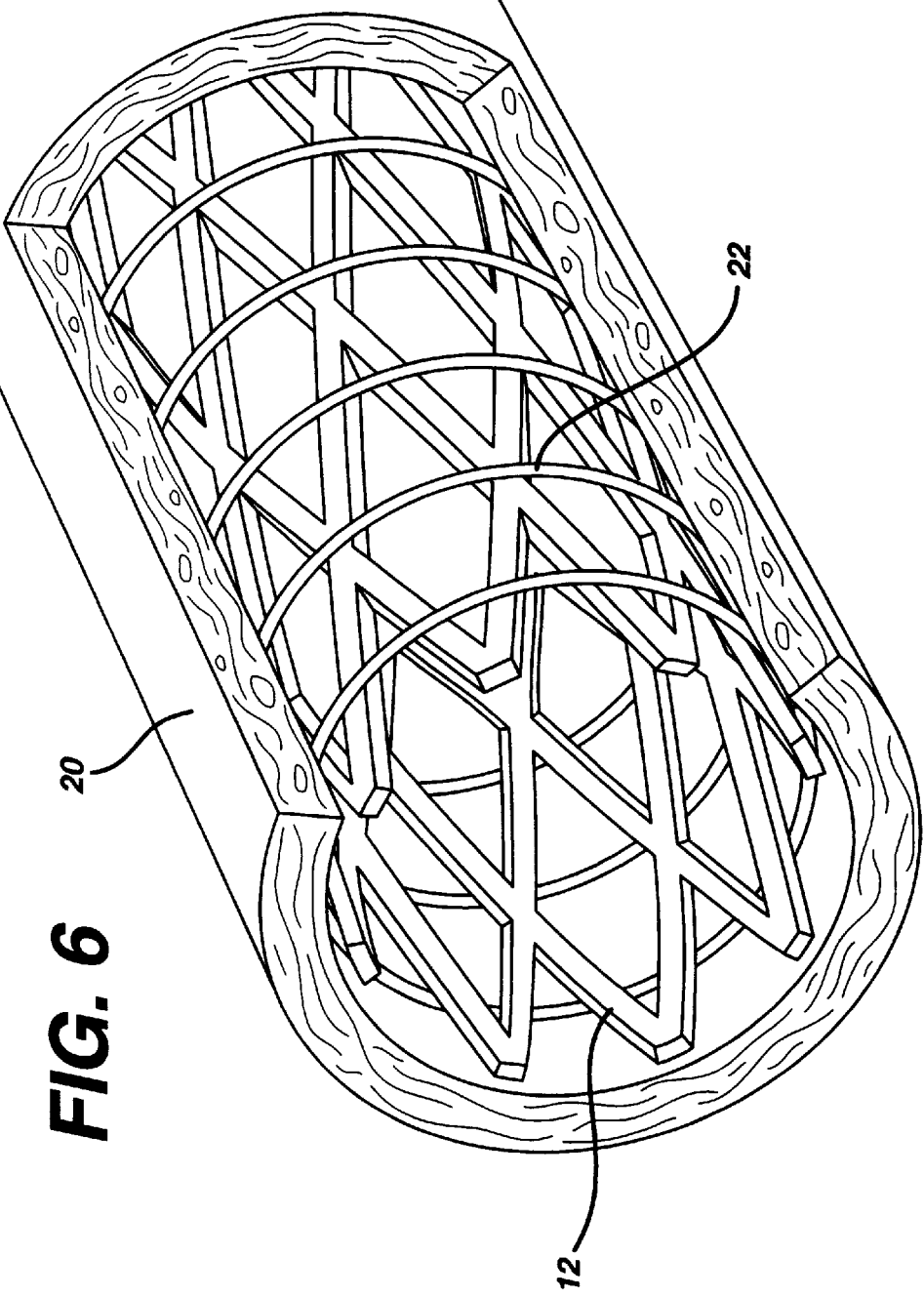
FIG. 6 is a similar drawing to that of FIG. 5, but showing an alternative embodiment of the present invention.

FIG. 6 shows a lumen 20 with a device according to the present invention located within it. The device comprises a stent sleeve as in the device described above with reference to FIGS. 1 to 5. The restraint 22 is discontinuous rather than being formed from a sheet as shown in FIG. 3. The restraint 22 comprises a plurality of substantially circumferential bands extending around the stent sleeve. The bands can be provided as separate bands, or as a single band wound helically around the stent sleeve.

What is claimed is:

1. A method for implanting a composite stent device within a lumen of a patient, said method comprising the steps of:

a. providing a composite stent comprising a tubular stent sleeve having a relaxed configuration, the stent sleeve made from a superelastic shape memory alloy such that the stent sleeve will exert an outward force when transversely constrained to a configuration smaller than the relaxed configuration, and a plastically deformable restraint element covering at least a portion of an exterior of the stent sleeve, the stent sleeve exerting an outward force on the restraint element, the restraint element having sufficient strength to prevent the stent sleeve from expanding to exert a force on a lumen of a vessel until plastic deformation of the restraint element by an expansion device; and b. inserting said composite stent within said lumen, deforming said composite stent towards said tubular stent sleeve's relaxed configuration by applying an outward force along an interior of said composite stent, and removing said outward force upon said composite stent making contact with an internal surface of said lumen.

2. A method as claimed in claim 1, in which the step of deforming said stent towards said tubular stent sleeve's relaxed configuration by applying an outward force along an interior of said stent comprises using an inflatable balloon and the method includes the step of inflating the balloon.

* * * * *